(12) United States Patent
Tanaka

(10) Patent No.: US 11,617,497 B2
(45) Date of Patent: Apr. 4, 2023

(54) WIRE-DRIVEN MANIPULATOR

(71) Applicant: CANON KABUSHIKI KAISHA, Tokyo (JP)

(72) Inventor: Yusuke Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 570 days.

(21) Appl. No.: 15/902,900

(22) Filed: Feb. 22, 2018

(65) Prior Publication Data
US 2018/0242820 A1    Aug. 30, 2018

(30) Foreign Application Priority Data
Feb. 28, 2017 (JP) .............................. JP2017-037714

(51) Int. Cl.
*A61B 1/005* (2006.01)
*A61B 1/00* (2006.01)
*G02B 23/24* (2006.01)

(52) U.S. Cl.
CPC .......... *A61B 1/0051* (2013.01); *A61B 1/0055* (2013.01); *A61B 1/0057* (2013.01); *A61B 1/00154* (2013.01); *G02B 23/24* (2013.01); *A61B 1/0008* (2013.01)

(58) Field of Classification Search
CPC . A61B 1/00154; A61B 1/0051; A61B 1/0055; A61B 1/0057; G02B 23/24
See application file for complete search history.

(56) References Cited

U.S. PATENT DOCUMENTS

| 5,174,277 | A | * | 12/1992 | Matsumaru | .......... | A61B 1/0055 |
| | | | | | | 600/142 |
| 5,531,664 | A | * | 7/1996 | Adachi | ................ | A61B 1/0058 |
| | | | | | | 600/149 |
| 2009/0062606 | A1 | * | 3/2009 | Ueda | .................. | A61B 1/00078 |
| | | | | | | 600/114 |
| 2009/0326325 | A1 | * | 12/2009 | Naito | ................... | A61B 1/0055 |
| | | | | | | 600/141 |
| 2016/0213227 | A1 | * | 7/2016 | Osaki | ................... | A61B 1/0057 |

FOREIGN PATENT DOCUMENTS

| JP | H02177931 | A | 7/1990 |
| JP | 2007527296 | A | 9/2007 |
| JP | 2007298815 | A | 11/2007 |
| JP | 2012518477 | A | 8/2012 |
| JP | 2012213438 | A | 11/2012 |
| JP | 7039174 | B2 | 3/2022 |

* cited by examiner

*Primary Examiner* — Aaron B Fairchild
(74) *Attorney, Agent, or Firm* — Canon U.S.A., Inc. IP Division

(57) ABSTRACT

A wire-driven manipulator includes a first member and a second member into both of which a flexible member is inserted, the second member being disposed more on a base end side than the first member, wherein the first and the second members are bent by a drive of the flexible member, wherein the first member includes a bonding portion mechanically bonded with the member, wherein the second member is independent of the first member and the member, and wherein a variation of an average curvature of the first member caused by a drive of the members is larger than a variation of an average curvature of the second member.

8 Claims, 14 Drawing Sheets

WIRE-DRIVEN MANIPULATOR

BACKGROUND

Field of the Disclosure

The present disclosure relates to a wire-driven manipulator usable for a bendable portion of an endoscope.

Description of the Related Art

In the field of endoscopic apparatuses, a flexible endoscope has been known. The flexible endoscope has a bendable portion provided at a distal end portion to be inserted into the body of a subject to enable an operator to bend the bendable portion. Japanese Unexamined Patent Application Publication No. 2007-527296 discusses a structure having lumens for storing control elements such as wires. Japanese Unexamined Patent Application Publication No. 2007-527296 discusses a structure in which a metal vertebra-shaped device is connected to a bendable portion to control the orientation of the bendable portion on the base end side. Japanese Patent Application Laid-Open No. 2007-298815 discusses a structure of a tube-shaped pipe sleeve for connecting a bendable portion and a flexible tube. However, when a flexible tube and a bendable portion are mechanically bonded as described above, a force for driving a wire in a push-pull way to bend the bendable portion is transmitted to the flexible tube via the bendable portion and a pipe sleeve. This force causes a deformation of the flexible tube and accordingly changes the orientation of a distal end of the flexible tube. As a result, the position and orientation of the bendable portion provided at the distal end of the flexible tube also change, producing an error in orientation control.

SUMMARY

The present disclosure has been devised, among other things, in view of the above-described problem, and to improving the accuracy in orientation control on a bendable portion.

According to an aspect of the present disclosure, a wire-driven manipulator includes a first member and a second member into both of which a flexible member is inserted, the second member being disposed more on a base end side than the first member, wherein the first and the second members are bent by a drive of the flexible member, wherein the first member includes a bonding portion mechanically bonded with the member, wherein the second member is independent of the first member and the member, and wherein a variation of an average curvature of the first member caused by a drive of the members is larger than a variation of an average curvature of the second member.

Further features of the present disclosure will become apparent from the following description of exemplary embodiments with reference to the attached drawings.

DESCRIPTION OF THE EMBODIMENTS

Exemplary embodiments of the present disclosure will be described below with reference to the accompanying drawings.

Figure 1A:
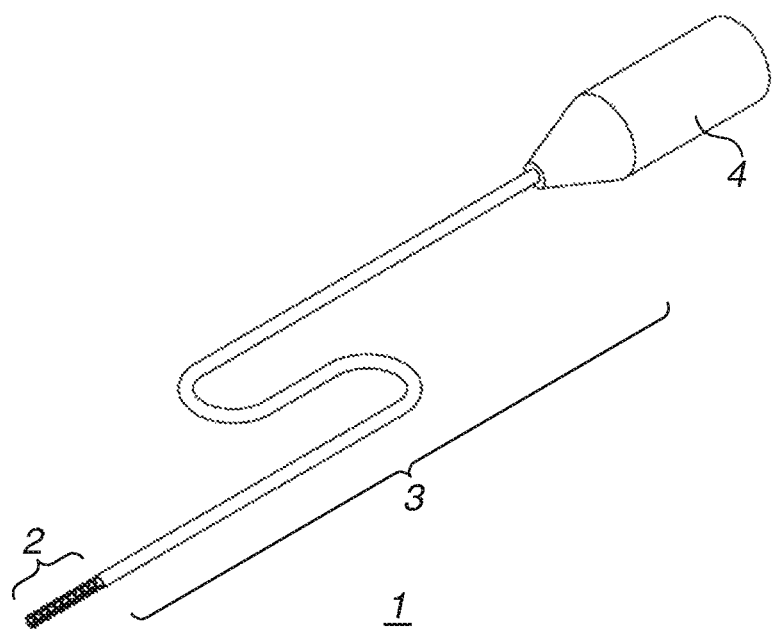
FIGS. 1A and 1B illustrate a configuration of a wire-driven manipulator according to a first exemplary embodiment of the subject disclosure.
Figure 1B:
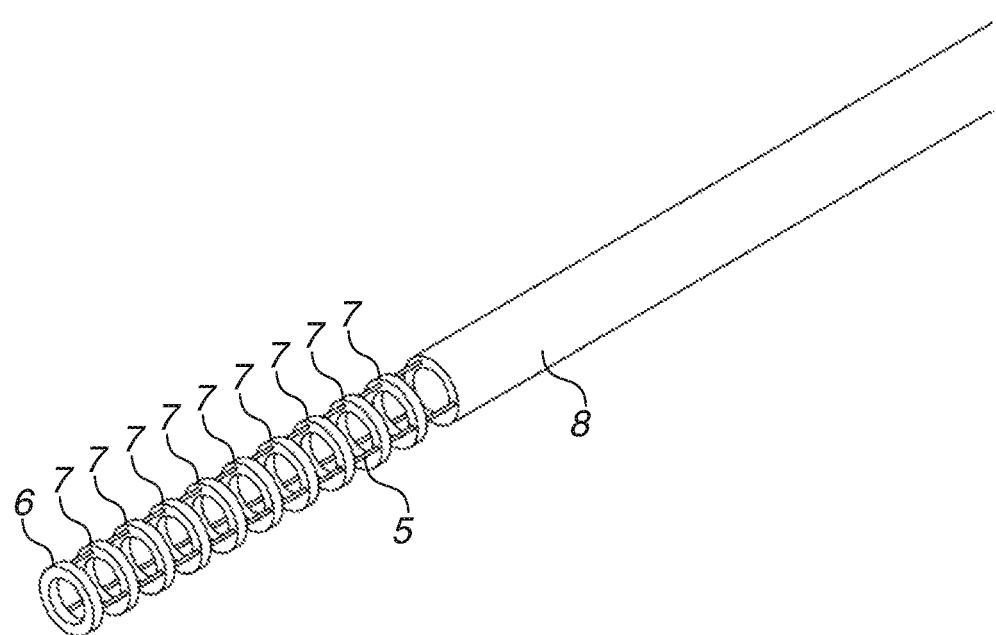

A wire-driven manipulator according to an exemplary embodiment of the present disclosure will be described below. FIG. 1A is a perspective view illustrating a configuration of a wire-driven manipulator 1 according to the present exemplary embodiment. FIG. 1B illustrates in more detail a configuration of a distal end portion of the wire-driven manipulator 1 illustrated in FIG. 1A.

The wire-driven manipulator 1 includes a bendable distal portion 2 which is deformable by the drive of a wire, a long bendable portion 3 which is flexible and passively deformable by an external force, and a base 4.

The bendable distal portion 2 is provided with a plurality of flexible members 5, a distal end member 6, and a plurality of guide members 7, as illustrated in FIG. 1B. The plurality of guide members 7 and the distal end member 6 are juxtaposed and concatenated via the members 5. The members 5 extend in the longitudinal direction of the bendable distal portion 2 as a first member. One end of each member 5 is bonded with the distal end member 6 via a bonding portion. The bonding portion bonds each member 5 to the distal end member 6 through adhesion, pinning, or screw clamp. The other end of each member 5 is bonded with the drive units 11 described below. Examples of the members 5 as flexible members include, for example, piano wires, stainless steel wires, nickel titanium alloy wires, or other metal wires, and strings. The distal end member 6 has an annular shape (annular ring) centering on an axis along the longitudinal direction of the bendable distal portion 2. The plurality of members 5 is bonded to the distal end member 6. Bondings are made through adhesion, pinning, screw clamp, or any other methods. More specifically, the bendable distal portion 2 has a configuration in which the distal end member 6 and the plurality of guide members 7 as annular members are juxtaposed by using the members 5 as concatenation members. The members 5 are bonded to the distal end member 6 provided more on the distal end side than the annular member closest to the base end side.

Figure 2:
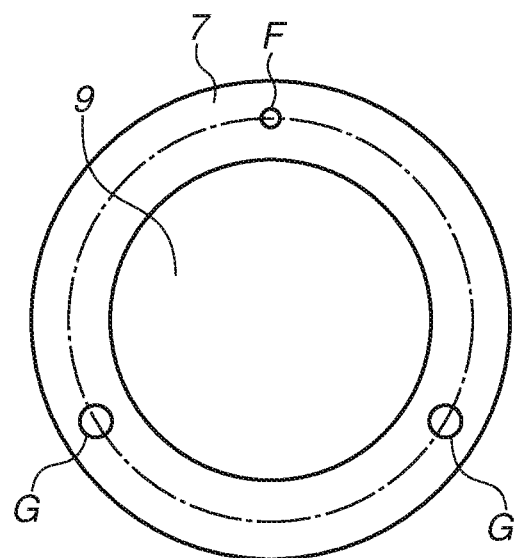
FIG. 2 is a cross-sectional view illustrating a guide member, according to one or more embodiment of the subject disclosure.

As illustrated in FIG. 2, each guide member 7 has a similar annular shape to the distal end member 6 and is provided with guide holes G for guiding the members 5. The guide holes G are provided so that the members 5 are inserted into them. At a fixing hole F, at least one of the members 5 is fixed to the guide member 7 through adhesion, pinning, or screw clamp. The other members 5 are slidable with respect to the corresponding guide holes G. The fixing hole F may have a smaller diameter than that of the guide holes G so that, when a member 5 is inserted, the fixing hole F and the member 5 are fixed with each other. The guide member 7 is made of a resin having a small friction coefficient since the guide member 7 contacts the members 5 via the guide holes G. In the bendable distal portion 2, since both the distal end member 6 and the guide members 7 have an annular shape, a tool such as an image sensor and a catheter can be inserted into the bendable distal portion 2 by using a lumen 9 serving as a hollow portion. The guide holes G and the fixing hole F are disposed on a concentric circle centering on the axis in the direction penetrating through the lumen 9. In particular, it is desirable that the guide holes G and the fixing hole F are disposed at equal angular intervals.

Figure 3:
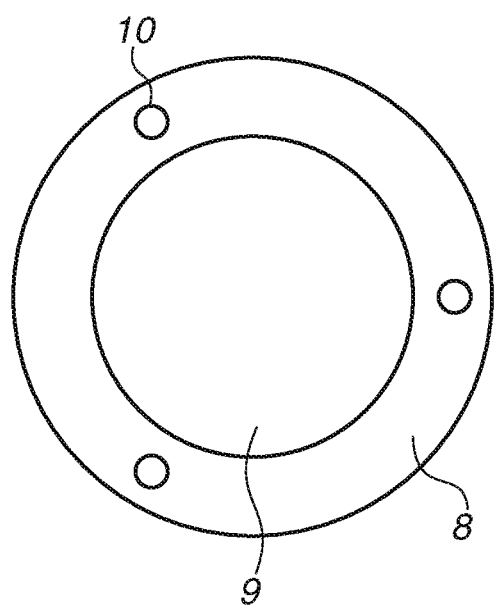
FIG. 3 is a cross-sectional view illustrating a multi-lumen guide tube, according to one or more embodiment of the subject disclosure.

The long bendable portion 3 as a second member according to the present exemplary embodiment includes a multi-lumen guide tube 8 as a multi-lumen tube with a cylindrical shape having the center axis in the longitudinal direction of the long bendable portion 3. FIG. 3 is a cross-sectional view illustrating the multi-lumen guide tube 8 in a plane perpendicularly intersecting with the longitudinal direction of the multi-lumen guide tube 8. The multi-lumen guide tube 8 includes the lumen 9 at the center, allowing a tool to be inserted thereinto in a similar way to the bendable distal portion 2. The multi-lumen guide tube 8 also includes a plurality of guide lumens 10 extending in the axial direction on the wall surface of a cylindrical member which determines the lumen 9. The members 5 are inserted into the guide lumens 10 which are configured to be slidable with respect to the members 5. In this configuration, when the members 5 passing through the guide lumens 10 are driven in the longitudinal direction, the members 5 transmit a force without buckling. The multi-lumen guide tube 8 is made of a resin having a small friction coefficient since the multi-lumen guide tube 8 contacts the members 5 via the guide lumens 10. In addition, a highly flexible material is used since the multi-lumen guide tube 8 is demanded to be bent and deformed by an external force. The long bendable portion 3 is not mechanically bonded with the bendable distal portion 2 as the first member. The long bendable portion 3 and the bendable distal portion 2 are independent of each other. The long bendable portion 3 is also independent of the members 5 which slide in the above-described guide lumens 10.

Figure 4:
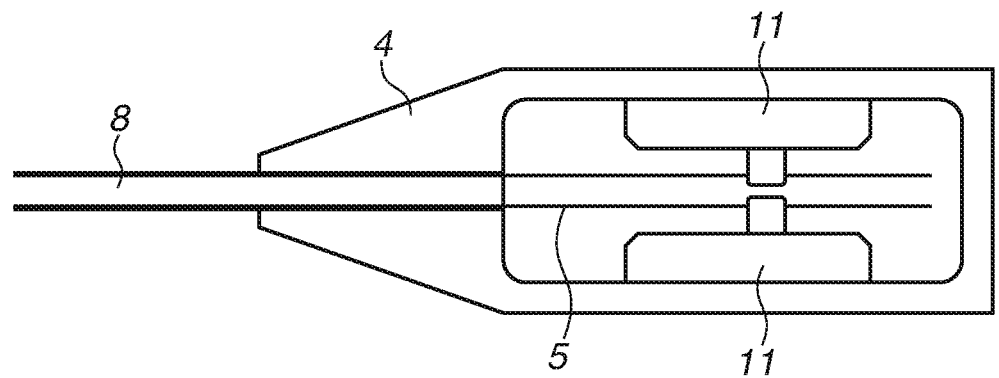
FIG. 4 illustrates an example configuration of a base, according to one or more embodiment of the subject disclosure.

FIG. 4 illustrates a structure of the base 4. The multi-lumen guide tube 8 is fixed to the base 4 through adhesion, pinning, or screw clamp. The base 4 includes drive units 11 to which the members 5 are connected. The drive units 11 are controlled by a control unit (not illustrated). Although, two drive units 11 are illustrated in FIG. 4, it is possible that one drive unit 11 is provided for each member 5 and horizontally drives each member 5 in a push-pull way.

A bending operation of the wire-driven manipulator 1 when the members 5 are driven will be described below. When the members 5 are driven in a push-pull way by using the drive units 11, the members 5 slide without buckling in the guide lumens 10 provided in the multi-lumen guide tube 8 in the long bendable portion 3. As a result, there arises differences in length between the members 5 within the section of the bendable distal portion 2. Since the members 5 are bonded with the distal end member 6, the differences in length of the members 5 at the bendable distal portion 2 cause a force in the bending direction, making it possible to bend the bendable distal portion 2, as illustrated in FIG. 5.

Figure 5:
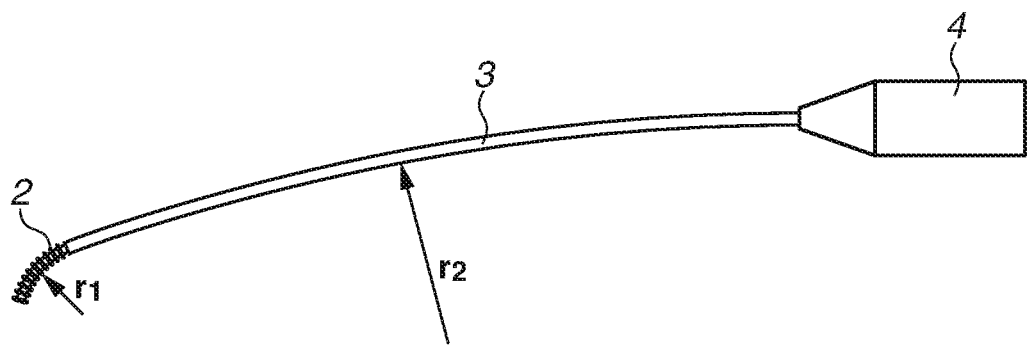
FIG. 5 illustrates a deformation when members of the wire-driven manipulator are driven, according to one or more embodiment of the subject disclosure.

FIG. 5 illustrates the wire-driven manipulator 1 in a bent state when viewed from the lateral side. When the drive units 11 drive the members 5, the bendable distal portion 2 and the long bendable portion 3 are deformed in a circular arc shape, providing a curvature radius of r1 and r2, respectively. It is desirable that the bendable distal portion 2 is easier to be deformed than the long bendable portion 3. The two portions are configured so that the relation between r1 and r2 is represented by formula 1.

$$r1 < r2 \qquad \text{(Formula 1)}$$

Although, in the example illustrated in FIG. 5, the bendable distal portion 2 and the long bendable portion 3 are deformed in a circular arc shape, the two portions are not necessarily deformed in a circular arc shape. In this case, the bendable distal portion 2 and the long bendable portion 3 may be designed so that the average curvature distribution $\rho 1$ of the bendable distal portion 2 and the average curvature distribution $\rho 2$ of the long bendable portion 3 are in the following relation:

$$\rho 1 > \rho 2 \qquad \text{(Formula 2)}$$

More specifically, as a result of driving the members 5 for bending the bendable distal portion 2, the long bendable portion 3 also bends. It is necessary to design the bendable distal portion 2 and the long bendable portion 3 so that the variation of the average curvature of the bendable distal portion 2 accompanying the drive of the members 5 is larger than the variation of the average curvature of the long bendable portion 3.

Although, referring to FIG. 1B, three members 5 are used to allow the bendable distal portion 2 to be bent in an arbitrary direction, the number of the members 5 is not limited thereto. For example, two members 5 may be used to allow the bendable distal portion 2 to be bent only in one plane, or four or more members 5 may be disposed to provide redundancy.

Figure 6:
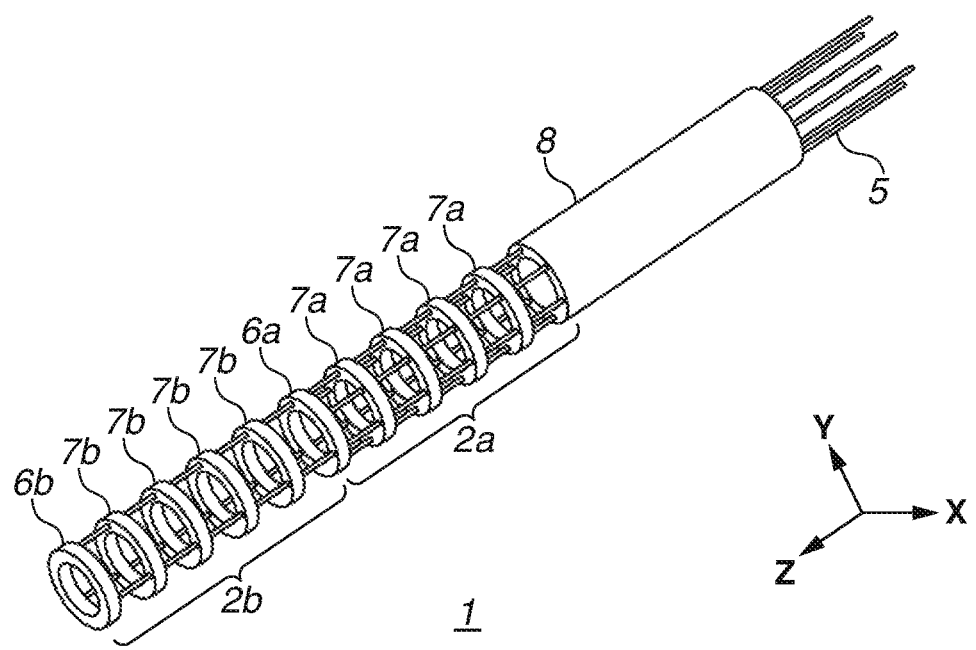
FIG. 6 illustrates a configuration of a wire-driven manipulator having a plurality of bendable distal portions, according to one or more embodiment of the subject disclosure.

Although a drive unit 11 is bonded to each member 5, at least one drive unit 11 required to planarly drive the bendable distal portion 2 or at least two drive units 11 are required to three-dimensionally drive the bendable distal portion 2. For example, assuming a case where three members 5 are provided for three-dimensional drive, it is not necessary to drive all of the three members 5 and therefore the members 5 may only be fixed to the base 4. More specifically, the base 4 may be provided with a fixing portion for fixing the member 5, or a support member may be provided as a different member from the base 4. As a method for fixing the members 5, adhesion, hooking on a projection such as a hook, and any other methods are usable. Although, referring to FIG. 1B, the bendable distal portion 2 includes only one bendable portion, the bendable distal portion 2 may include a plurality of bendable distal portions 2a and 2b, as illustrated in FIG. 6. In this example, three members 5 are associated with each of the bendable distal portions 2a and 2b. One of the three members 5 associated with each bendable distal portion is bonded with the guide members configuring the associated bendable distal portion, and is configured to be slidable with respect to the guide holes of the distal end member and the guide members of the unassociated bendable distal portion. The remaining two members 5 are bonded only with the distal end member of the associated bendable distal portion, and are configured to be slidable with respect to the guide holes of the distal end member and the guide members of the other (unassociated) bendable distal portion. In addition, three or more bendable distal section portions 2 may be provided.

In the structure of the wire-driven manipulator 1 according to the present exemplary embodiment, the bendable distal portion 2 and the long bendable portion 3 are independent of each other without being directly fixed to each other. In a case where the bendable distal portion 2 and the long bendable portion 3 are directly fixed with a pipe sleeve as in the structure discussed in Japanese Patent Application Laid-Open No. 2007-298815, driving the members 5 in a push-pull way transmits a compressing force or tensile force applied to the members 5 to the long bendable portion 3 via the bendable distal portion 2, bending the long bendable portion 3. As a result, the orientation of the distal end of the long bendable portion 3 changes to cause an error in orientation presumption and control on the bendable distal portion 2. Therefore, using a structure in which no force is transmitted between the bendable distal portion 2 and the long bendable portion 3 as in the present exemplary embodiment enables improving the accuracy in orientation presumption and control on the distal end shape of the bendable distal portion 2.

A wire-driven manipulator 1 according to a second exemplary embodiment of the present disclosure will be described below with reference to FIGS. 7 to 10. The present exemplary embodiment differs from the first exemplary embodiment in that a long bendable portion 3 is composed of a plurality of parts.

Figure 7:
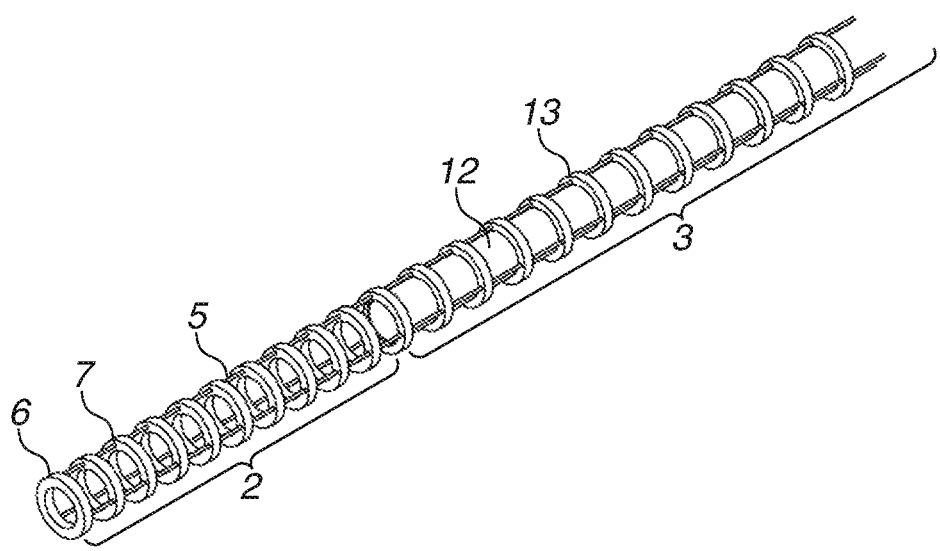
FIG. 7 illustrates a configuration of a wire-driven manipulator according to a second exemplary embodiment of the subject disclosure.
Figure 8:
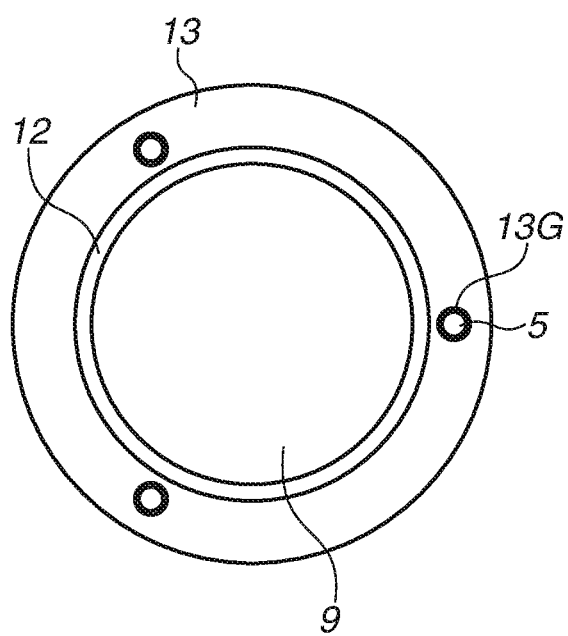
FIG. 8 illustrates a cross-section including a long portion guide member, according to one or more embodiment of the subject disclosure.

As illustrated in FIG. 7, the long bendable portion 3 includes a main tube 12 and long portion guide members 13. FIG. 8 illustrates a cross-section including a long portion guide member 13. The main tube 12 has a tubular structure including a lumen 9 at the center similar to the multi-lumen guide tube 8. Each of the long portion guide members 13 is provided with guide holes 13G for guiding members 5 which are disposed to be inserted into the guide holes 13G. The long portion guide members 13 make it possible to transmit the displacement to the bendable distal portion 2 while maintaining the positional relation of each member 5. In other words, it is assumed that the guide holes 13G provided on the wall surface that determines the lumen 9 of the multi-lumen guide tube 8 according to the first exemplary embodiment are replaced by the long portion guide members 13 according to the present exemplary embodiment. The long portion guide members 13 are fixed to the main tube 12 at predetermined intervals through adhesion, pinning, or screw clamp to enable guiding the members 5 without being buckled when the members 5 are driven in a push-pull way. The long portion guide members 13 are made of a resin having a small friction coefficient since the long portion guide members 13 contact the members 5 via the guide holes 13G.

Figure 9:
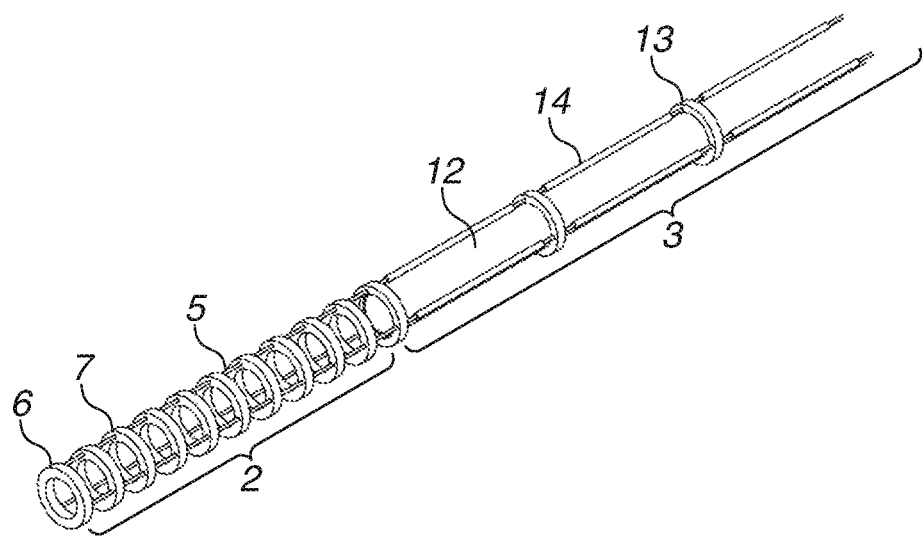
FIG. 9 illustrates an example configuration of the wire-driven manipulator according to the second exemplary embodiment of the subject disclosure.

Referring to FIG. 8, the long bendable portion 3 includes the main tube 12 and the long portion guide members 13. Referring to FIG. 9, guide tubes 14 for guiding the members 5 are disposed between the long portion guide members 13. The members 5 are disposed to be slidably inserted into the guide tubes 14. Disposing the guide tubes 14 enables reducing the number of the long portion guide members 13. The guide tubes 14 are fixed to the main tube 12, for example, through adhesion. The guide tubes 14 are made of a resin having a small friction coefficient since the guide tubes 14 contact the members 5.

Figure 10A:
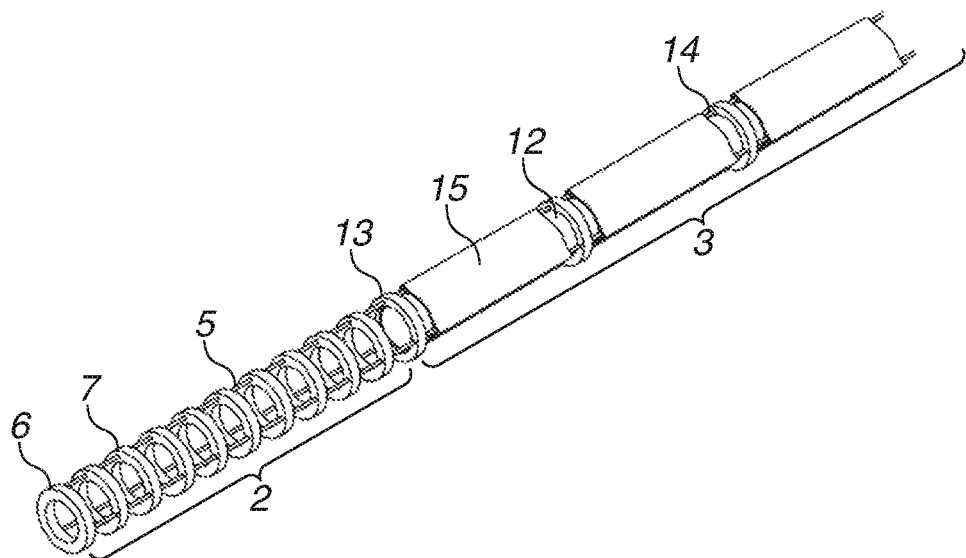
FIGS. 10A and 10B illustrate another example configuration of the wire-driven manipulator according to the second exemplary embodiment of the subject disclosure.

FIG. 10A illustrate an another method for fixing the guide tubes 14 to the main tube 12. Referring to FIG. 9, the guide tubes 14 are fixed to the main tube 12. In a configuration illustrated in FIG. 10A, the guide tubes 14 are fixed by guide tube protection members 15.

Figure 10B:
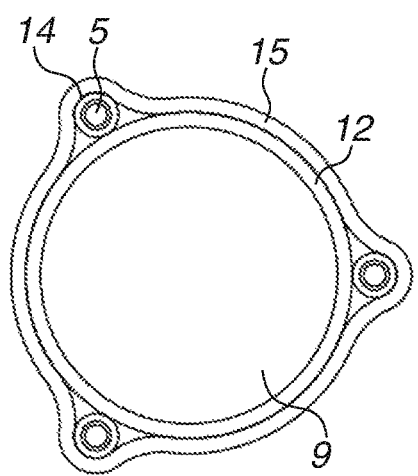

FIG. 10B illustrates a cross-section including a guide tube protection member 15. The guide tubes 14 disposed around the main tube 12 are fixed to the circumference of the main tube 12 by the guide tube protection member 15. The guide tube protection member 15 holds the guide tubes 14 to prevent the positional relation between the guide tubes 14 from being changed. In this case, the guide tubes 14 do not need to be adhered to the main tube 12, and the guide tubes 14 and the main tube 12 may be slidable with each other in the axial direction of the main tube 12. The guide tube protection member 15 may press-fit the guide tubes 14 to the main tube 12, for example, by using a flexible heat contraction material or an adhesive protection material. Although, referring to FIG. 10A, one guide tube protection member 15 is disposed between the long portion guide members 13, a plurality of guide tube protection members 15 having a shorter length in the longitudinal direction may be disposed between the long portion guide members 13.

Referring to FIG. 10A, a minute gap is provided between a long portion guide member 13 and a guide tube 14. When the long bendable portion 3 is bent by an external force, this configuration enables preventing the guide tubes 14 from being deformed by a compressing force through the contact between the long portion guide members 13 and the guide tubes 14.

A similar effect to that in the first exemplary embodiment can also be acquired through the configurations according to the present exemplary embodiment.

Figure 11A:
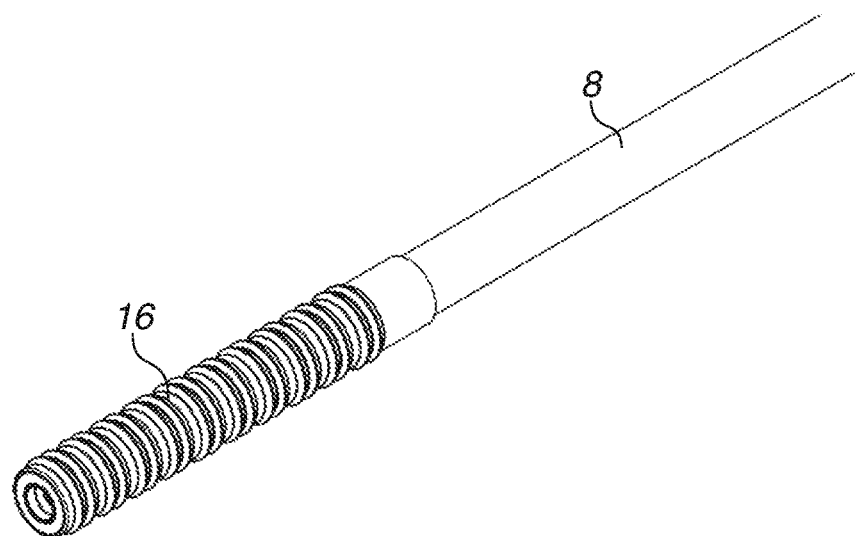
FIGS. 11A and 11B illustrate an example configuration of a wire-driven manipulator according to a third exemplary embodiment of the subject disclosure.
Figure 11B:
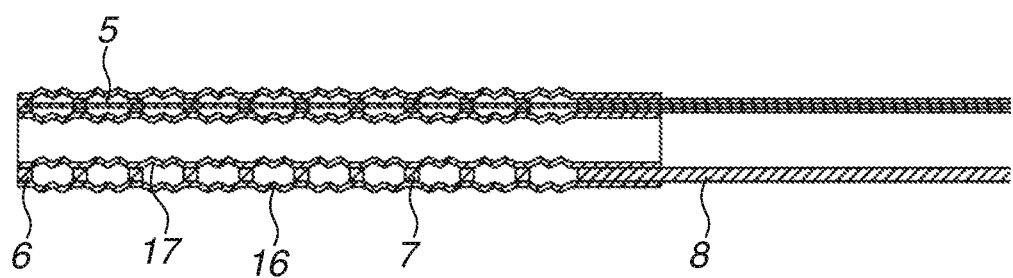

A wire-driven manipulator 1 according to a third exemplary embodiment of the present disclosure will be described below with reference to FIGS. 11A to 13B. The wire-driven manipulator 1 illustrated in FIG. 11A is provided with a distal outer skin 16 and a distal inner skin 17 for covering the bendable distal portion 2. FIG. 11B is a cross-sectional view illustrating the wire-driven manipulator 1 illustrated in FIG. 11A.

The distal outer skin 16 and the distal inner skin 17 respectively cover the outer and the inner surfaces of the distal end portions of the members 5, the distal end member 6, the guide members 7, and the multi-lumen guide tube 8 to provide a function of protecting the wire-driven manipulator 1 and a function of reducing friction thereof. The distal outer skin 16 and the distal inner skin 17 have a flexible structure such as a bellows-like resin structure and are made of a low elastic material such as rubber. The distal outer skin 16 and the distal inner skin 17 are fixed at one or more positions on the distal end member 6 and the guide members 7. The distal outer skin 16 and the distal inner skin 17 may be integrally formed with the distal end member 6 and the guide members 7. Further, the distal outer skin 16 and the distal inner skin 17 may be integrally formed. In this case, the integration enables thinning the bendable distal portion 2. In addition, the distal outer skin 16 and the distal inner skin 17 may be detachably attached to the bendable distal portion 2. It is desirable that the bending rigidity of the distal outer skin 16 and the distal inner skin 17 is sufficiently smaller than that of a structure composed of the members 5, the distal end member 6, and the guide members 7 so that these skins do not disturb the bending action of the bendable distal portion 2. The distal outer skin 16 and the distal inner skin 17 are in slidably contact with the distal end portion of the multi-lumen guide tube 8. This makes it possible, also when the bendable distal portion 2 is bent, to reduce the transmission of a reactive force from the bendable distal portion 2 to the long bendable portion 3, improving the driving accuracy.

Although, in the above-described example, the distal outer skin 16 and the distal inner skin 17 are fixed to the bendable distal portion 2, the distal outer skin 16 and the distal inner skin 17 may be fixed to the long bendable portion 3 and slidably in contact with the bendable distal portion 2.

Figure 12:
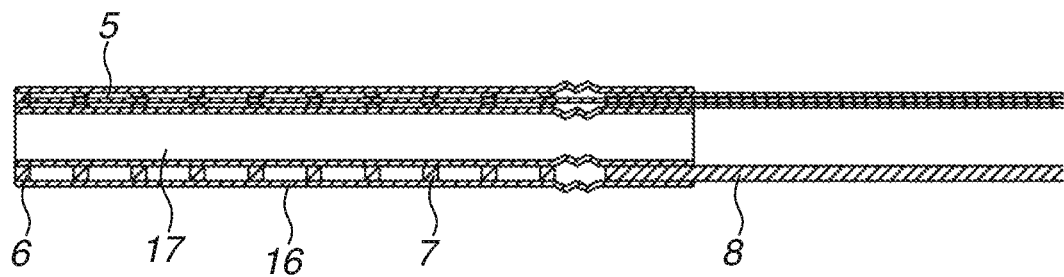
FIG. 12 is a cross-sectional view illustrating a distal outer skin and a distal inner skin, according to one or more embodiment of the subject disclosure.

FIG. 12 illustrates examples of the distal outer skin 16 and the distal inner skin 17 having different shapes from those illustrated in FIG. 11B. The distal outer skin 16 and the distal inner skin 17 are formed of a flexible elastic material, and have a bellows structure at the boundary portion between the bendable distal portion 2 and the long bendable portion 3. The distal outer skin 16 and the distal inner skin 17 are designed so that the rigidity of the boundary portion is lower than that of other portions. This design enables reducing the transmission of a reactive force from the bendable distal portion 2 to the long bendable portion 3. The boundary portion between the bendable distal portion 2 and the long bendable portion 3 is not limited to a bellows structure, and may have any other structures having lower rigidity than the boundary portion. The rigidity may be lowered by forming the boundary portion with a material different from the materials of other portions. When the rigidity of the distal outer skin 16 and the distal inner skin 17 of the boundary portion between the bendable distal portion 2 and the long bendable portion 3 is sufficiently lower than that of the structure of the bendable distal portion 2 including the members 5, the distal end member 6, and the guide members 7, the distal outer skin 16 and the distal inner skin 17 may be fixed to the distal end portion of the multi-cavity guide tube 8 through adhesion.

Figure 13A:
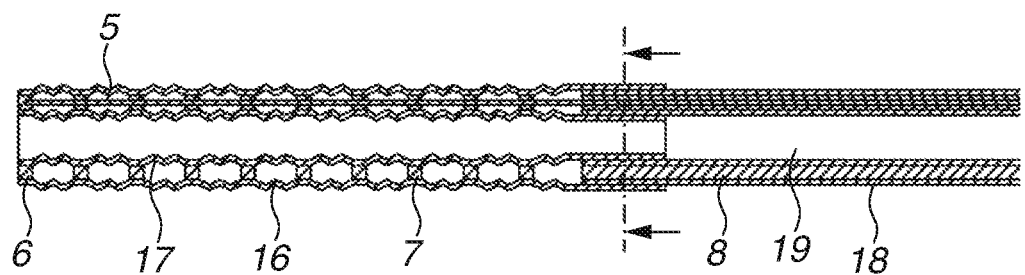
FIGS. 13A and 13B are cross-sectional views illustrating a distal outer skin and a distal inner skin, according to one or more embodiment of the subject disclosure.
Figure 13B:
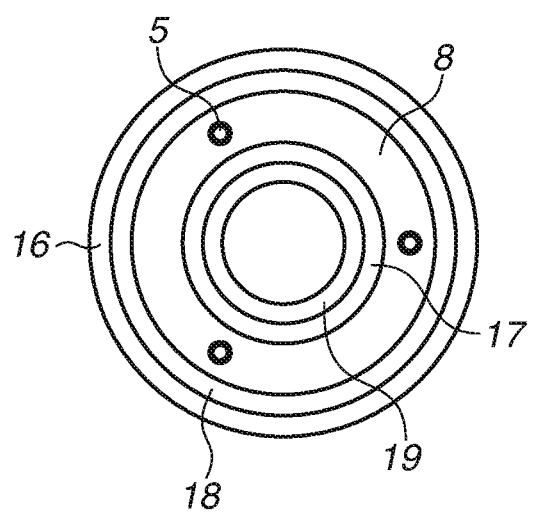

FIG. 13A is a cross-sectional view illustrating a configuration of a wire-driven manipulator 1 having not only a distal outer skin 16 and a distal inner skin 17 but also a long outer skin 18 and a long inner skin 19. FIG. 13B illustrates a section in the plane indicated by the arrows illustrated in FIG. 13A. As illustrated in FIG. 13A, the wire-driven manipulator 1 is provided with the long outer skin 18 and the long inner skin 19 having a function of protecting the multi-lumen guide tube 8 and a function of reducing friction thereof. As illustrated in FIG. 13B, in the vicinity of the distal end portion of a multi-lumen guide tube 8, the distal outer skin 16 is overlapped with the long outer skin 18, and the distal inner skin 17 is overlapped with the long inner skin 19 so that the boundary portion is not exposed. The distal outer skin 16, the long outer skin 18, the distal inner skin 17, and the long inner skin 19 are made of a material having a small friction coefficient so that the distal outer skin 16 and the long outer skin 18, and the distal inner skin 17 and the long inner skin 19 are respectively slidable with each other.

Alternatively, when the rigidity of the distal outer skin 16 and the distal inner skin 17 is sufficiently low as described above, the distal outer skin 16 and the long outer skin 18, and the distal inner skin 17 and the long inner skin 19 may be respectively fixed with each other through, for example, adhesion. In addition, the distal end member 6, the guide members 7, the distal outer skin 16, the distal inner skin 17, the long outer skin 18, and the long inner skin 19 may be integrally formed as long as the above-described functions are maintained. Although, in the example illustrated in FIG. 13A, the wire-driven manipulator 1 has the multi-lumen guide tube 8, the present exemplary embodiment is also applicable to a structure including the main tube 12, the long portion guide members 13, the guide tubes 14, and the guide tube protection members 15 according to the second exemplary embodiment, instead of the multi-lumen guide tube 8.

A similar effect to that in the first exemplary embodiment can also be acquired through the configuration according to the present exemplary embodiment.

Figure 14:
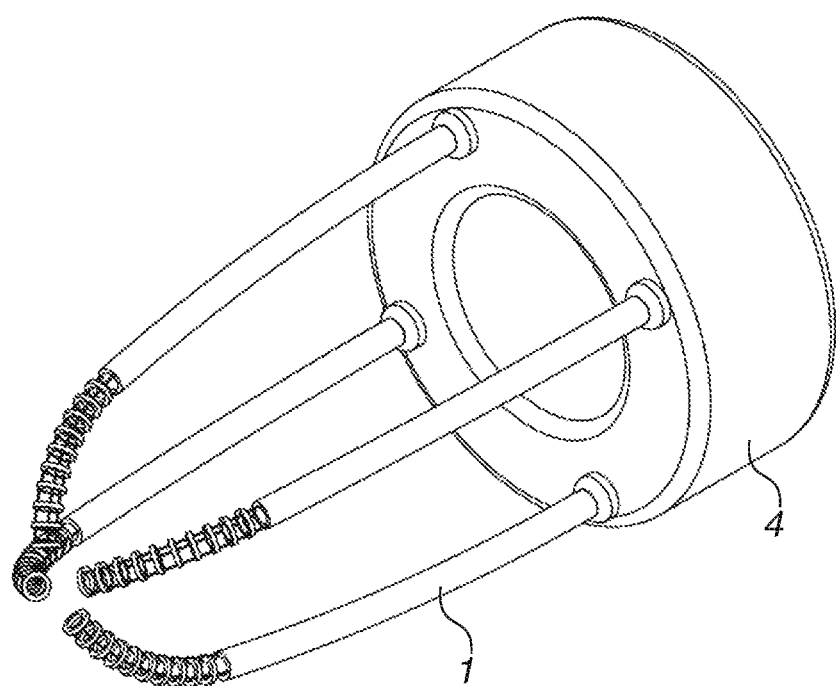
FIG. 14 illustrates an example configuration of a wire-driven manipulator according to a fourth exemplary embodiment of the subject disclosure.

Although, in the first to the third exemplary embodiments, the wire-driven manipulator 1 is applied to such an apparatus as an endoscope, the application of the wire-driven manipulator 1 according to the present disclosure is not limited thereto. A fourth exemplary embodiment is a robot hand using wire-driven manipulators. FIG. 14 illustrates a robot hand 20 according to the present exemplary embodiment. The robot hand 20 is provided with a plurality of wire-driven manipulators 1 on a base 4. The robot hand 20 grasps and manipulates an object by driving a plurality of the wire-driven manipulators 1. Distal ends of the wire-driven manipulators 1 are provided with an image sensor, pressure sensor, and temperature sensor, making it possible to grasp and manipulate an object while observing it. The configurations of the wire-driven manipulators 1 according to the first to the third exemplary embodiments are applicable to the wire-driven manipulators 1 mounted on the robot hand 20 according to the present exemplary embodiment. In addition, a plurality of the wire-driven manipulators 1 may be configured to be detachably attached to the base 4 and exchangeable according to use.

While the present disclosure has specifically been described based on the above-described specific exemplary embodiments, the present disclosure is not limited thereto but can be modified in diverse ways without departing from the technical concepts thereof, and a plurality of exemplary embodiments can be combined.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present disclosure, it is possible to provide a wire-driven manipulator which is advantageous in improving the accuracy in orientation control on a bendable portion.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2017-037714, filed Feb. 28, 2017, which is hereby incorporated by reference herein in its entirety.

What is claimed is:

1. A wire-driven manipulator comprising:
    a base;
    a distal bendable section including a first bonding portion and a plurality of guide members wherein adjacent guide members of the plurality of guide members are separated from each other to create a gap between the adjacent guide members;
    a following bendable section disposed between the distal bendable section and the base and including a second bonding portion and a plurality of guide members wherein adjacent guide members of the plurality of guide members are separated from each other to create a gap between the adjacent guide members;
    a long bendable section disposed between the following bendable section and the base;
    a distal wire having one end bonded to the first bonding portion, being inserted into the plurality of guide members of the distal bendable section, the following bendable section, and the long bendable section, and having an other end guided to the base;
    a following wire having one end bonded to the second bonding portion, not being inserted into the plurality of guide members of the distal bendable section, being inserted into the plurality of guide members of the following bendable section and the long bendable section, and having an other end guided to the base; and
    a drive unit configured to drive the distal wire and the following wire,
    wherein the wire-driven manipulator is configured such that the distal bendable section is bent by driving the distal wire and the following bendable section is bent by driving the following wire,
    wherein the distal bendable section is covered by an outer skin and a bending rigidity of the outer skin is smaller than a bending rigidity of a structure composed of the distal wire, the first bonding portion and the plurality of guide members of the distal bendable section.

2. The wire-driven manipulator according to claim 1, wherein the long bendable section includes a cylindrical member, and
    wherein the distal wire and the following wire are inserted into the cylindrical member along a wall surface of the cylindrical member in an axial direction.

3. The wire-driven manipulator according to claim 2, wherein the cylindrical member is a multi-lumen tube having a plurality of lumens extending in the axial direction, and
    wherein the distal wire and the following wire are is inserted into the plurality of lumens.

4. The wire-driven manipulator according to claim 1, wherein the distal bendable section is covered by an inner skin and a bending rigidity of the inner skin is smaller than a bending rigidity of a structure composed of the distal wire, the first bonding portion and the plurality of guide members of the distal bendable section.

5. The wire-driven manipulator according to claim 4, wherein the inner skin and the outer skin are fixed on the first bonding portion.

6. The wire-driven manipulator according to claim 4, wherein the inner skin is fixed at one or more positions on the plurality of guide members of the distal bendable section.

7. The wire-driven manipulator according to claim 1, wherein at least three distal wires are bonded to the first bonding portion,
    wherein at least two of the at least three distal wires are driven to bend the distal bendable section and at least one of the at least three distal wires is not driven to bend the distal bendable section.

8. The wire-driven manipulator according to claim 1, wherein the drive unit is configured to drive the distal wire in a push-pull way to bend the distal bendable section.

* * * * *